United States Patent [19]

Dunn

[11] 3,961,896
[45] June 8, 1976

[54] ANALYSIS OF NITRILE SYNTHESIS GAS STREAMS

[75] Inventor: Bobby Eugene Dunn, Murray, Ky.

[73] Assignee: The B. F. Goodrich Company, Akron, Ohio

[22] Filed: Nov. 28, 1975

[21] Appl. No.: 635,963

Related U.S. Application Data

[62] Division of Ser. No. 500,802, Aug. 26, 1974, which is a division of Ser. No. 291,741, Sept. 25, 1972, abandoned.

[52] U.S. Cl. .............................. 23/232 R; 23/254 R; 260/465.3; 23/230 A
[51] Int. Cl.² ................. G01N 33/00; C07C 121/04
[58] Field of Search .......... 23/232 R, 232 C, 254 R, 23/230 A; 260/465.3; 73/23 R

[56] References Cited
UNITED STATES PATENTS

| | | | |
|---|---|---|---|
| 2,955,457 | 10/1960 | Peters et al. | 73/23 |
| 3,308,151 | 3/1967 | Callahan | 260/465.3 |
| 3,512,393 | 5/1970 | Weiss | 73/23 |
| 3,529,937 | 9/1970 | Ihara et al. | 23/232 R X |
| 3,589,171 | 6/1971 | Haley | 23/232 C X |
| 3,673,854 | 7/1972 | Manka | 73/23 |

*Primary Examiner*—Morris O. Wolk
*Assistant Examiner*—Arnold Turk
*Attorney, Agent, or Firm*—J. Hughes Powell, Jr.

[57] ABSTRACT

Gas streams flowing in a nitrile synthesis plant, and particularly the hot reactor effluent gases, are analyzed by a new method wherein sample gas streams are filtered and temperature conditioned in the range from about 350° to about 450°F. before being passed to a gas analyzer instrument, preferably a mass spectrometer. With the latter instrument the conditioned stream of gas is passed continuously through the ion source assembly throughout the mass scan period, a mode of operation which assists in reducing lag in analysis to very little more than gas transit times. The mass spectrometer generates peaked direct current electrical signals which can be peak detected and amplified in a linear fashion to drive a direct-reading recorder instrument or such signals can be interfaced with a digital computer for programmed computation and readout of gas stream composition. The rapidity, reliability and accuracy of the analysis provides accurately calibrated control of the nitrile synthesis wherein a 1-monoolefin such as propylene or isobutylene are blended with ammonia and oxygen or air and passed through a bed of solid ammoxidation catalyst. Operation of such process in response to such analysis permits hitherto impractically low molar feed ratios of ammonia:olefin of 1.03 to 1.07:1 and high excess effluent oxygen levels of 4 to 7 mol % in the reactor effluent gases without significant losses in nitrile yield or significantly increased levels of oxygenated by-products.

3 Claims, 7 Drawing Figures

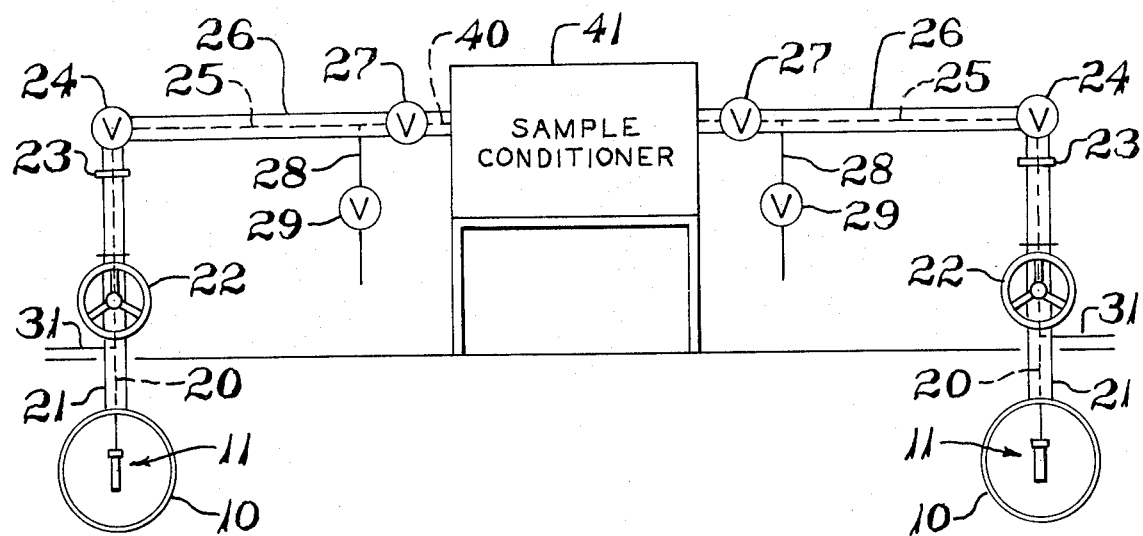
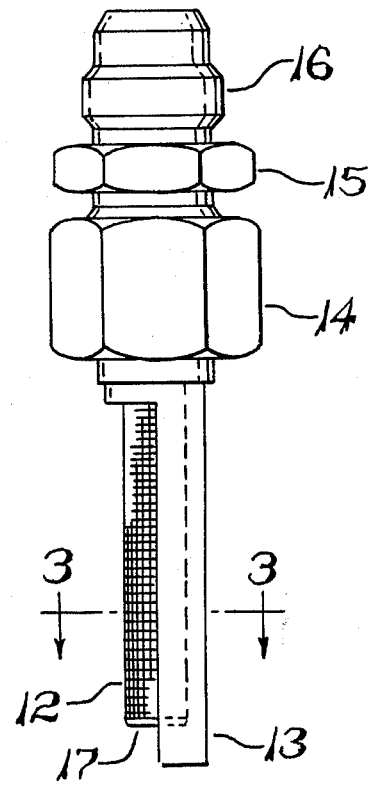
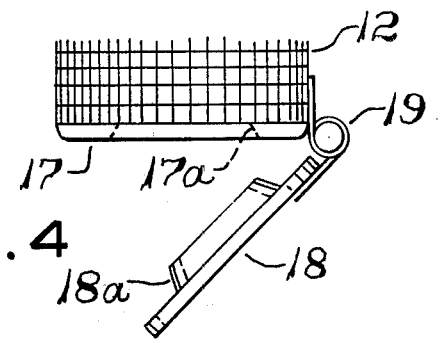
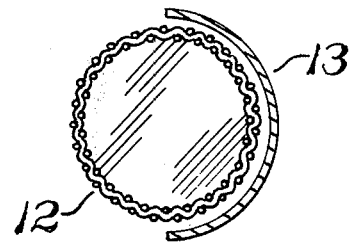

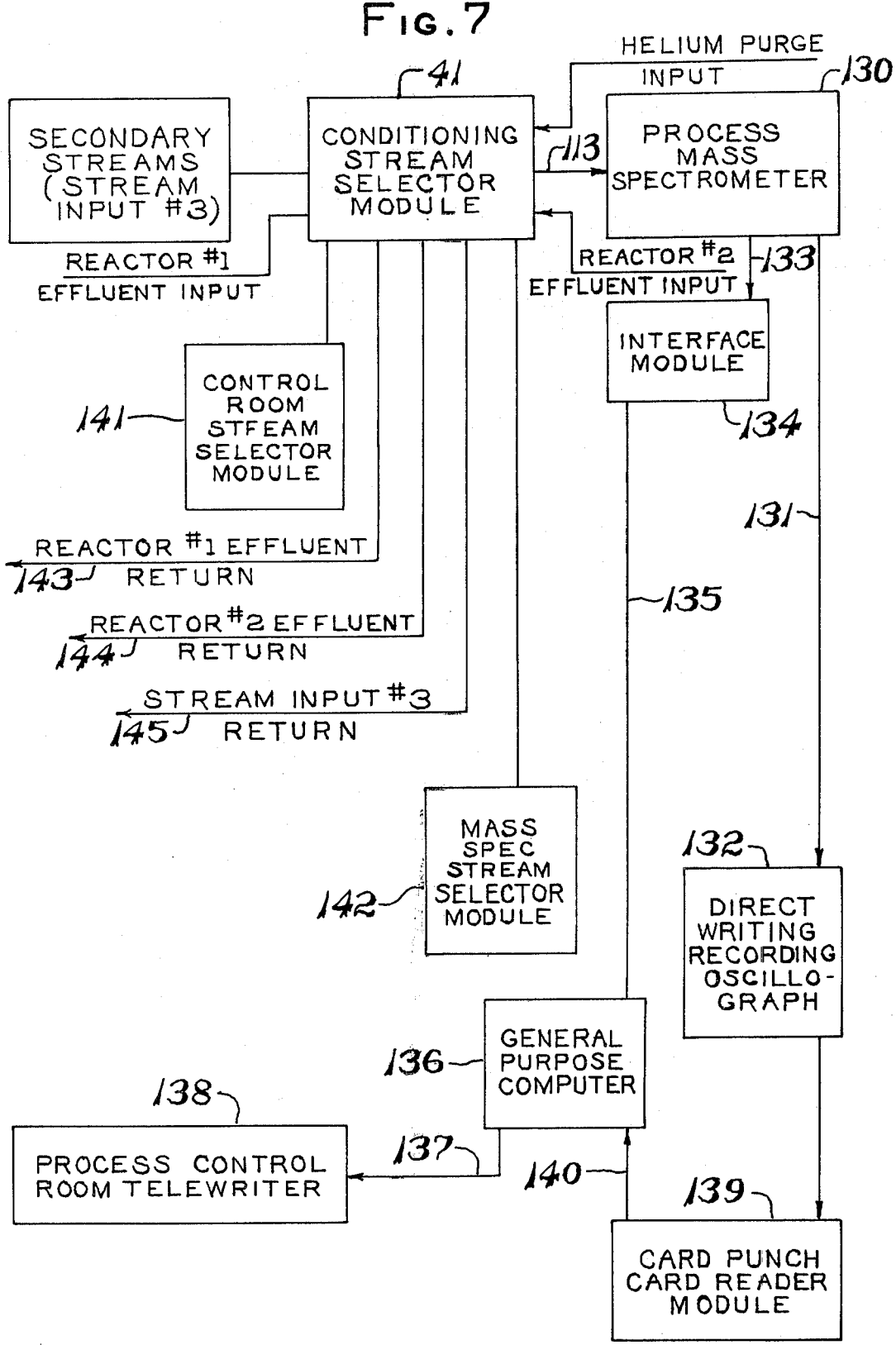

ANALYSIS OF NITRILE SYNTHESIS GAS STREAMS

CROSS REFERENCE TO RELATED APPLICATIONS

This application is a division of application Ser. No. 500,802 filed Aug. 26, 1974 which in turn is a division of application Ser. No. 291,741 filed Sept. 25, 1972, now abandoned.

BACKGROUND OF INVENTION

The present invention relates generally to the nitrile synthesis wherein a mixture of an aliphatic alphamonoolefin such as propylene or isobutylene, ammonia and oxygen are interacted over a solid ammoxidation catalyst at elevated temperature producing an unsaturated aliphatic nitrile such as acrylonitrile from propylene or methacrylonitrile from isobutylene. More specifically, the invention relates to an improvement in the control of such synthesis allowing most accurate control of the input gas stream and the accurate and fast determination of conversion, selectivity and yield not only of the desired nitrile product but also of unreacted feed materials and/or by-products some of which are accurate telltales of correct or incorrect operation. Most specifically, the invention relates to an effluent gas sampling, gas sample conditioning and gas analysis system.

PRIOR ART

U.S. Pat. No. 3,308,151 discloses the synthesis of, acrylonitrile or methacrylonitrile, by the catalytic oxidation of, respectively, propylene/ammonia or propylene-isobutylene mixtures, in the presence of oxygen over solid catalysts containing a catalytically-active complex of the crystalline oxides of antimony and uranium. The latter catalyst is of the type disclosed also in U.S. Pat. No. 3,198,750 and U.S. Pat. No. 3,341,471. Other catalysts for this same process are based on iron, on iron nad antimony and on bismuth. The type of reaction is sometimes referred to as an ammoxidation reaction. In the U.S. the ammoxidation process presently is carried out in a fluid bed reactor employing a supported version of the Sb/U oxide catalyst carried in or on a granular support such as silica. The disclosure of U.S. Pat. Nos. 3,308,151, 3,198,750 and 3,341,471 are incorporated by reference herein for the purpose of the catalyst and process disclosures.

While successfully employed on a large scale in many large commercial plants in many countries, the process suffers from significant and long-existing control deficiencies most of which appear to be traceable (1) to the lack of sensitivity, accuracy and/or calibration stability of available gas flow control instruments and (2) lack of adequate gas analysis systems which will accurately reveal process performance. The process operator seldom is able to control with the required precision for any appreciable period of time the relative molar ratios of the three ingredient feed gases being fed to the catalyst nor has he been able to determine sufficiently quickly the results of any readjustment of the input feed mixture, pressure, reaction temperatures, contact time, or any other process variable.

The only method of evaluating operating results have been the "recovery run procedure" wherein a sample of reactor effluent gases are collected, the gases scrubbed with water, condensibles removed, and the various liquids and noncondensible gases thus obtained laboriously analyzed in a chemical laboratory. Such a procedure usually requires 4 to 8 hours for completion including a laborious computation of results and, as a result, only a very limited number of determinations per week per reactor can be made. Moreover, the results are available to the process operator much too long after they are really needed to be truly useful. Thus, undesired trends in process operations take days and perhaps even weeks to be detected and corrected. The laborious recovery run procedure, moreover, is not sufficiently sensitive nor accurate to reveal subtle changes and/or trends in process operation.

The Sb/U catalysts have proven to be quite prone to reduction with attendant loss in nitrile conversion selectivity. Also, the selectivity of these catalysts has proven to be much more dependent on the state of oxidation of the catalyst than was originally believed. Lack of control over input feed streams has resulted in occasional intermittent or continuous reduction of catalyst which in a matter of months requires complete change-out of catalyst for return of expensive catalysts (ca $2.65/lb) to the catalyst manufacturer for high temperature regeneration. As a result, catalyst costs including catalyst consumption, regeneration expense and a larger than desirable inventory of catalyst have been far too high.

As a result, nitrile plants seldom have operated for long with catalysts at their optimum state of oxidation which produces highest olefin conversion and highest nitrile selectivity to the desired nitrile product.

The state of oxidation of the preferred Sb/U catalysts, when referred to herein, is as determined according to the XRD and ESR techniques of Charles J. Carman and William J. Kroenke, as set forth in their copending application, Ser. No. 288,775 filed Sept. 13, 1972.

Heretofore, many attempts have been made to harness various types of gas analysis instruments to monitor the input and/or effluent gas streams of the nitrile process. The analysis of the effluent gas streams has been especially unsatisfactory due to the pronounced tendency of such effluent gases to carry over catalyst fines and to generate oily and/or glass-like organic solids which not only plug small sample lines and/or the expensive instruments themselves but also the solids formed have altered the gas composition as read by the instrument. As a result, process operators have usually employed gas analyzers in the effluent gas system only after quench and/or other recovery or purification steps have been performed where the instruments do not read the gas composition at the reactor exit but rather report the composition of a residual "scrubbed" gas stream. Such analytical results not only lag the reactor quite seriously but also have to be adjusted or back-calculated to a supposed reactor effluent composition which will be correct largely only by happenstance. A double back-calculation by material balance techniques has been necessary to arrive at an apparent reactor feed input composition. The errors and very considerable lag in such procedures are obvious.

The nitrile synthesis is in need of a better mode of operational control which will provide process operators with speedier, more frequent, more reliable, and much more detailed and more accurate information on process performance by means of a speedy, reliable and accurate means for determining meaningful input feed and reactor effluent compositions.

SUMMARY OF INVENTION

The present invention relates generally to the synthesis of unsaturated aliphatic nitriles from an alphaolefin, ammonia and oxygen. More specifically the invention relates to an improved method of controlling such nitrile synthesis. Most specifically, the invention relates to a method of, and apparatus for, analyzing nitrile effluent gas compositions.

In the present invention, a stream of the reactor effluent gases from the nitrile synthesis is filtered and temperature-conditioned to a temperature in the range of from about 350° to about 450°F to produce a clean, stable stream of gas for analysis. Solids borne by the raw effluent stream as it leaves the reactor are removed by such treatment. Also, solids formed in the stream during conditioning are also removed. When properly so conditioned, the stream does not appear to form solids at an appreciable rate since the lines, filters, valves, and other equipment carrying conditioned gases remain clean for appreciable periods. Since most gas analytical instruments employ small sample input lines, often as small as capillary lines, I have found it necessary to employ filter means capable of removing all solids at least as small as about 5 microns in diameter. Better yet, I prefer to employ filters capable of retaining or removing all solids larger than about 1 micron in diameter. As will appear hereinbelow, most preferred is to employ several filters in series of progressively smaller aperture or pore sizes to effect a stepwise removal of solids. In the latter most preferred embodiment, the smallest pore size filter capable of retaining solids in the 1 to 2 micron size is employed at the analytical instrument inlet to serve as a guard filter.

The gases in a bed of catalyst will be at a temperature in the range of 800° to 950°F but will be at a somewhat lower temperature when they leave the reactor, depending on reactor design (i.e. fixed bed vs fluid bed), reactor cooling design, feed preheater interchange design and many other factors. In my experience with efficient fluid bed reactors employing interchange of heat between the outgoing effluent and the incoming feed materials, such affluent gases will be in the range of 400° to 500°F with 450° to 500°F being the most common. Such gases do not require appreciable cooling to reach a temperature in the conditioning range recited herein in which case conditioning consists in supplying heat to maintain the temperature in the range. With other reactor designs and different operating modes, the situation may be otherwise. When so conditioned, however, I have found that the effluent gases may be conducted considerable distances of 30 to 50 meters or more in small temperature-controlled lines of the sampling circuits without appreciable solids formation. Most importantly, I have found that increasing the line lengths does not affect gas composition or impair the validity of their analysis, providing care is exercised to maintain the temperature of the gases at a reasonably constant temperature in the range recited throughout that portion of the sampling system up to the analytical instrument.

A separate gas sampling flow circuit is set up for the effluent gas stream of each reactor. Since the quantity of gases in each circuit is extremely small in relation to the throughput of a large commercial reactor, the flow of gases is preferably continuously maintained in each circuit to minimize surface and the equilibration effects and have a representative gas sample available for analysis at any time while the reactor is operating. While each reactor effluent circuit may be returned to the process downstream of the sampling location, there is a greater pressure drop in the sampling circuit than in the main process lines, due to smaller sample line size, which would require pumping to effect return. Since the relatively small material losses makes the return of unused sample gases uneconomic, I have merely fed the combined unused sample gases to a suitable waste disposal system.

While I do not wish to be limited by theory, it is believed that prior difficulties encountered in analyzing nitrile reactor effluent gases have been due to the interaction on cooling of the small amounts of HCN present therein with the inherent water content of the gases formed during reaction and/or introduced in the air employed as the source of oxygen. HCN and $H_2O$ are believed to interact with the formation of organic cyanohydrin polymers and/or condensates which congeal in the gas stream and deposit in the gas sample lines and/or in the analytical instruments causing unreliable and unsatisfactory analytical performance. Such polymeric solids do not appear to be formed at appreciable rates in the temperature range of 350° to 450°F.

The highly preferred mass spectrometer generates, in seriatim, a peaked direct current electrical signal corresponding to the mass of each constituent gas flowing in the gas sampling circuit in question, starting at the gas constituent of lowest mass and progressing upwardly in mass to the constituent having the greatest mass. In the present invention, the presence or absence and concentration of as many as eighteen constituents of a nitrile reactor effluent gas stream is thus determined. The amplitude or voltage of each such peaked signal generated by the spectrometer is directly proportional to the proportion of the particular gaseous constituent in question in the sample gases. Such electrical signals can be sensed or peak-detected and evaluated in any way such as simple peak detection and linear amplification to furnish drive to a direct recording oscillograph bearing a chart calibrated in voltage (proportion) versus mass (or constituent).

A more sophisticated approach is to feed the electrical signals from the mass spectrometer to a suitably designed electronic interface scanning unit, which interface unit generates a series of digital binary coded number signals readable as mass number and concentration by a digital control computer programmed to compute from such coded number signals a complete analysis. While not necessarily a portion of the present invention, the digital control computer preferably is programmed to integrate in material balance fashion from an effluent gas composition analysis an exceptionally accurate input feed gas composition corresponding thereto. The thus calculated input gas composition has proven to be most accurate due to the fact that total materials accountability in the effluent analysis of this invention is in the range of 99% or better.

In the analytical method of this invention, a single gas analyzer instrument can provide analyses of the effluent from two or more adjacent nitrile reactors when a suitable gas flow switching means such as that shown in FIGS. 4 and 5 of the drawings herein is provided to connect the instrument to the desired sampling circuit.

Due to the rapidity with which analyses can be made by the method and apparatus of this invention, the process operators can bring a reactor on stream and line it out in a matter of a few hours or change the operating level and reestablish equilibrium in a similarly short period. This ability rapidly to reach equilibrium makes it possible for the operators to take a reactor out of operation, as for a catalyst air blow or minor equipment repair, at much more frequent intervals without large losses of production capacity. As a result, it is possible to operate each reactor at or near peak efficiency for an appreciably higher proportion of total operating time than has hitherto been possible.

Still further, the proportion of certain constituents of the effluent gases, for example acrolein versus carbon oxides and excess oxygen vs acrolein and carbon oxides, as also are unreacted feed gases, are direct telltales of the efficiency of the conversion of olefin to nitrile and of the degree of completion of the ammoxidation reaction. By observing these telltales and readjusting feed ratios, flow rates, hold-up times, reactor pressure, reaction temperatures, etc., the process operator is able very effectively to "fine tune" the process to maximize the production of the desired nitrile product and minimize olefin losses as carbon oxides and/or other more complex oxygenated by-products.

Also, such accurate knowledge of process performance indicates equipment malfunctions quite quickly allowing speedy correction.

Most importantly, however, I have found that such frequent and accurate determinations of process operation quickly reveals any reduction of the catalyst which may be occurring or which may have occurred since even slight catalyst surface reduction will show up as a loss in nitrile selectively as read by means of the yield of nitrile product and proportions of the various by-products formed. Such early and reliable detection of catalyst reduction enables the process operator to rectify same by temporarily increasing the proportion of oxygen fed, or in cases of somewhat more serious catalyst surface reduction, by shutting off the olefin and ammonia feeds and subjecting the catalyst bed to an air blow treatment for 1 to 24 hours at reactor temperatures of from about 420° to about 500°C. in order to burn off carbonaceous and/or organic residues on the catalyst and reoxidize the surface of the catalyst. Still more serious reduction of catalyst not confined to the surface or its immediate crystallographic environment requires heating in air at temperatures higher than can be attained in a nitrile reactor and this requires removing the catalyst for high temperature regeneration. The precise and knowledgeable control afforded by the method of this invention all but eliminates occurrence of the latter type of catalyst reduction. The actual life of the Sb/U catalysts under this improved method of control is unknown since elimination of the need for high temperature regeneration also eliminates the small but significant loss of catalyst surface area suffered in each high temperature regeneration treatment.

I have further found that the improved control provided by this invention permits a sizable reduction in ammonia per pound of product nitrile fed to the reactor. Whereas, U.S. Pat. No. 3,308,151 does not indicate precisely an optimum ammonia:olefin molar feed ratio, the patent recommends that such ratio should be between 1:1 and 5:1 leaving the implication that at least a substantial excess of ammonia over the olefin would be desirable. The latter implication is strengthened by most of the examples of the patent wherein a $NH_3$:propylene molar volume feed ratio of 1.5:1.0 is illustrated.

While it is doubtful that many commercial process users employ such a large excess of ammonia, the use of even a small excess of ammonia requires the unreacted residual ammonia to be scrubbed from the inert residual gases employing sulfuric acid before such residual gases are released to the atmosphere. The cost of such acid and of the disposal of crude ammonium sulfate produced is appreciable. I have found surprisingly that only a very, very small excess of ammonia over that actually consumed by the reaction can be employed without significant loss in olefin conversion or selectivity, providing, one compensates by simultaneously and significantly increasing the molar feed ratio oxygen:olefin. Here again U.S. Pat. No. 3,308,151 on the subject of oxygen proportions is not particularly helpful, since the patent text recommends a wide range $O_2$:olefin molar feed ratios between 1:1 to 3:1 but the examples show molar volume oxygen:propylene feed ratios of ca 2.6:1 (Ex. 1–4 and Examples 9 and 10) and ca 2.2 (Examples 5 and 6). Again it is doubtful whether commercial acrylonitrile reactors operating with air as a source of oxygen employ so large an excess of oxygen due to inert gas loading and/or losses of the expensive olefin as carbon oxides.

I have found that the $NH_3$:propylene molar feed ratio can be reduced to as low as 1.03:1 with the most desirable operation being secured in the range from about 1.03 to 1.07:1. With the latter ammonia:propylene ratios, it is necessary to increase the oxygen fed to the process to maintain high conversion and selectivity. Oxygen can be and is consumed in side reactions such as in burning of carbon and organic deposits on the catalyst and also in oxidizing the catalyst. For these and other reasons dependence upon the $O_2$:olefin feed ratio as a control is not wise. Rather, one should be concerned with the proportion of oxygen at the locus of the nitrile-forming reaction, i.e. in the catalyst bed. The most reliable indicator of the latter is the proportion of excess oxygen in the effluent gases. At least 4 mol % of excess or unreacted oxygen should appear in the reactor effluent gas stream to insure adequate oxygen for all consumption and, equally of importance, to maintain a high state of oxidation in the catalyst. Better yet, I have found it desirable to maintain between about 4 and about 7 mol % of excess oxygen in the reactor effluent gas stream when operating with $NH_3$:propylene mol ratios of from about 1.03 to about 1.07. I have found that the 4 to 7% oxygen content as read by the mass spectrometer is equivalent to 6 to 9% of excess oxygen as read by more conventional process oxygen analyzers operating on scrubbed, noncondensible effluent gases.

At the latter $NH_3$:propylene and $O_2$:propylene ratios savings in sulfuric acid consumption and crude ammonium sulfate disposal costs amounting to 0.15 to 0.3 cent/lb. of acrylonitrile produced have been realized. When so doing, the acrylonitrile process suffers not more than a 2% loss in propylene-to-acrylonitrile conversion over the maximum occasionally obtainable at higher $NH_3$:olefin molar feed ratios.

Such low ammonia/high oxygen operation has at its most important advantage better maintenance of the expensive Sb/U catalyst in a high state of oxidation where selectivity is highest.

Moreover, I have found that the sampling circuit of this invention, including all of the gas flow lines, the filters and valves can be maintained in clean, operable condition by an occasional backflushing with steam at a temperature of at least 250°F, and preferably between about 250° and 500°F. Apparently the steam is able to hydrolyze or otherwise decompose, loosen and remove the organic solids, carbon and/or catalyst fines, and/or sticky liquids from the lines, valves, and filters facilitating their removal from the circuit.

To reduce lag in the sampling circuit and the time required for the sampling circuit and switching circuits to come to equilibrium, I have found it desirable to size the sample flow lines to be relatively large compared to the analytical instrument input line and to ensure that the gas flows continuously therein at an appreciable rate in the circuit. Since many analytical instruments employ quite small input lines (the mass spectrometer input can be a 7mm capillary tube), the entire sampling flow circuit can be constructed of metal or glass tubing of ¼-inch to ⅜-inch sizes. As indicated, each of the reactor effluent sampling circuits, including its associated filters and switching valves, should be maintained at a conditioning temperature in the range recited.

DESCRIPTION OF DRAWINGS

FIG. 1 is a view in elevation, partly in section, showing the installation of the gas sampling and conditioning apparatus of this invention installed in the reactor effluent discharge lines of two adjacent nitrile reactors of commercial size;

FIG. 2 is a vertical plan view of a shielded filter probe assembly two of which are shown installed in the reactor effluent lines of FIG. 1;

FIG. 3 is a view in section taken along the section line 3 — 3 of FIG. 2;

FIG. 4 is a partial side view in elevation showing an optional spring-loaded end cap arrangement for the filter element of the probe assembly of FIGS. 1 to 3;

FIG. 7 is a block functional diagram showing in schematic fashion the interconnections between the sampling and conditioning circuits, the mass spectrometer analyzer, the remote stream selector control modules, the direct reading oscillograph, and the computer interface unit, computer and manual card punch data feed modules employed in an illustrative complete system for analysis of gas streams in a commercial nitrile plant employing two reactors.

SPECIFIC DESCRIPTION

Figure 5:
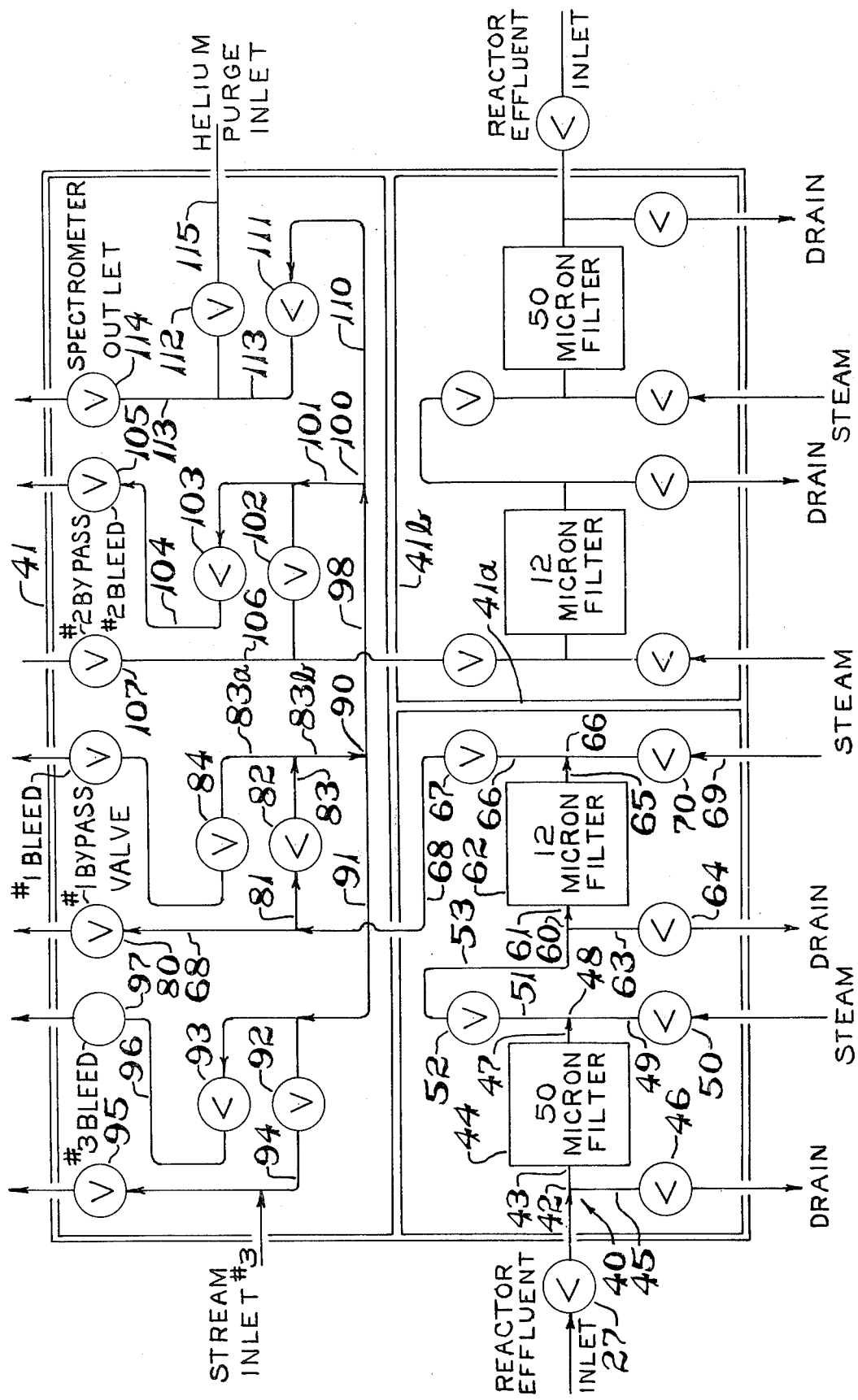
FIG. 5 is a top view, shown with cover removed, of the filter/switching box appearing in FIG. 1, the figure representing by means of arrows the direction of flow of sample gases from Reactor No. 1 Effluent Inlet to the Spectrometer Outlet.

The invention will be better understood by reference to the drawings, starting with FIG. 1 in which two reactor effluent gas sampling and conditioning circuits are arranged to serve two adjacent nitrile reactors. Since the installation portrayed in the figure is the same for each reactor only the section to the left of an imaginary vertical center line of FIG. 1 will be described but like reference numerals are affixed to the same elements on the right side of such center line.

Only the large reactor effluent discharge line 10 is shown with the rest of the reactor installation being deleted for clarity. Direction of gas flow is normal to and upwardly out of the plane of the drawing. A shielded filter probe assembly 11 is suspended at about the center of line 10, FIG. 1 showing such probe assembly as it appears from the downstreamside of the probe location.

Such probe assembly 11 is shown in FIGS. 2 and 3 to consist of the tubular or cylindrical wire screen filter element 12 protected on the upstream side with a half-circumferential, nonporous metal shield element 13 to shed gas borne solids, both such elements being held in spaced relation by a collar 14 and nut assembly 15. Also carried by the nut assembly 15 is an integral male tubing coupling fitting 16 adapted to mate with a female tubing coupling fitting (not shown) carried by the line to which the probe assembly 11 is attached. The filter element 12 as shown in FIG. 2 is made of a rigid wire screen having screen openings in the range of 50 to 100 microns in diameter and having a closed end 17 confining the filtering area to the tubular side portion of the filter element protected by shield 13. The shield element 13 protects the screen filter element 12 against direct impingement of gas borne catalyst solids and reduces the accumulation of the latter on the screen. Gas which penetrates the wire screen element 12 is relatively free of gas borne catalyst solids.

The wire screen filter element 12 alternatively may have, see FIG. 4, in its end element 17 a tapered hole 17a over which is fitted a cap 18 having a tapered seal element 18a which fits closely in hole 17a. The cap 18 is secured to the filter element 12 by a spring-loaded hinge assembly 19. Pressure of purge steam within the filter element 12 in excess of the strength of the spring-loaded hinge 19 will force the cap element open permitting a more unrestricted discharge of steam and purged liquids and solids. Another equivalent of the spring-loaded hinge is fitting the cap 18 of FIG. 4 on a spring-biased plunger carried concentrically within the cylindrical filter element 12. A spring-loaded filter element will sometimes avoid the necessity to remove the filter probe assembly 11 for cleaning should an abnormal accumulation of material enter, or be formed in, the sampling system.

The filter probe assembly 11 is attached to a gas sample tubing 20 which is supported within a protective outer casing consisting of an integral port fitting 21 and various pipe fittings and flanges, none of which are of significance except a gate valve 22 through which line 20 extends and which is in the fully-opened position when tubing 20 is in place but which can be closed when tubing 20 is withdrawn for cleaning, inspection and/or maintenance of the probe assembly 11. The outer casing is capped at its upper end by a tapped flange cover 23 which supports tubing 20 and serves as a support for a normally-open right angle valve 24. From the valve 24 a second length of gas supply tubing 25 extends through an outer insulated casing 26 to a normally-open valve 27 and a steam purge line 28 connected to a source of steam (not shown) having a normally-closed valve 29. Likewise, the space between tubing elements 20, 25 and their outer casings 21, 26 can be supplied with steam introduced through a fitting 31 for purge purposes and/or heating the sample lines 20, 25.

The entire outer casing from port fitting 21 to valve 27 and all of the interconnecting fittings preferably are enclosed in insulation (not shown) which can contain steam or electrical heat tracing as indicated above. Thus, all of tubing sections 20, 25 and their associated valves and fittings are maintained at the desired gas conditioning temperature in the range of from about 350° to about 450°F.

Figure 6:
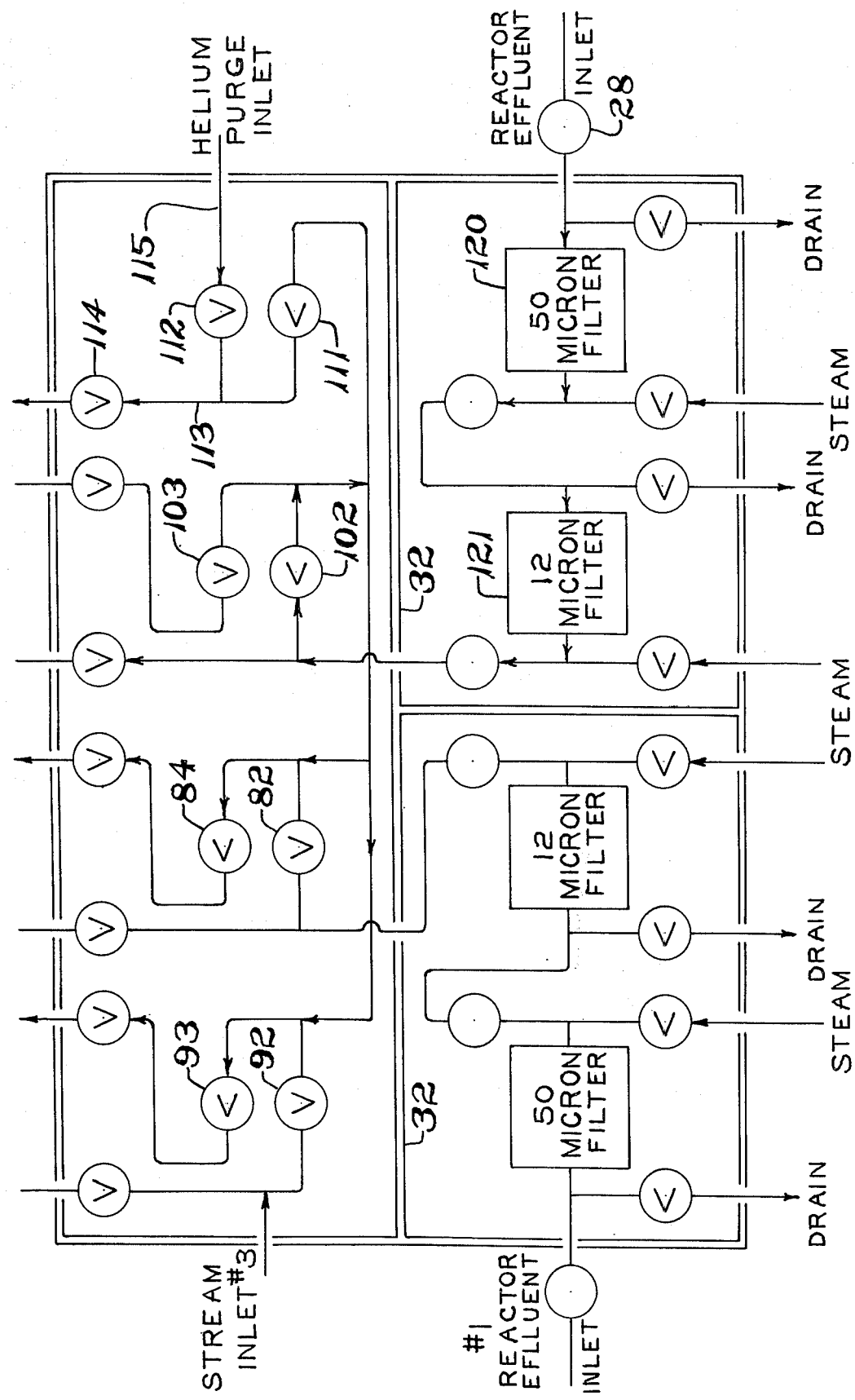
FIG. 6 is a view similar to that of FIG. 5 but showing the direction of gas flow when the gases entering through Reactor No. 2 Effluent Inlet are being fed to the analytical instrument.

Tubing 25 connects through normally-open valve 27 and and a nipple 40 with a filter/switching box or oven 41 the internal details of which are shown in FIGS. 5 and 6. Oven 41 likewise should be provided with heating means (not shown) and enclosed in a jacket of heat insulated material to inhibit heat loss. Actually, although not shown in the drawings, box oven 41 is provided with thermostatically-controlled electrical resistance heaters to maintain the entire box 41 and its contents at an essentially constant temperature. Preferably, such electrical heaters are arranged in three groups, one for each compartment of the box, i.e. one for Reactor No. 1 Inlet and its associated filters, lines, etc., similarly one for Reactor No. 2 Inlet, and the third for the upper valve compartment, all of which are described more fully below.

Referring now to FIG. 5 of the drawings, it will be seen that box 41 is divided by a vertical internal wall 41a and a horizontal wall 41b into three compartments, one filter compartment in the lower left quadrant of the figure associated with Reactor No. 1 Effluent Inlet, a second filter compartment in the lower right quadrant associated with Reactor No. 2 Effluent Inlet, and one across the top of the box wherein are housed the switching valves. Stream Inlet No. 3 enters the upper left side of the switching compartment directly, this Inlet being employed for process streams other than Reactor effluent gases since only the latter require filtering. A Helium Purge Inlet also enters the switching compartment on the right side of the upper switching compartment, the latter Inlet providing helium gas for instrument purge purposes as will be explained below. Stream Inlet No. 3 when utilized can be connected manually to any process stream by operating manual valves (not shown) or by flexible hose couplings in patch-panel style. In the installation represented in the drawings, the markedly lower frequency of use of the system for analysis of gas streams other than reactor effluent, for example reactor feed gas mixtures, vent gas analysis, etc., made it uneconomic to provide a complicated electric or electronically-controlled switching mechanism handling all streams in the plant.

Reactor effluent gases flow continuously into and out of box 41 entering through Reactor Effluent Inlets No. 1 and No. 2 whenever the corresponding reactors are operating. Such continuous flow of sample gases in each sampling circuit ensures equilibrium conditions between the gases and the equipment and a continuously-available clean and stable supply of gases ready for analysis.

When an analysis of the gases leaving Reactor No. 1 is required, the operator presses the appropriate selector push button in the Control Room Stream Selector Module (see description in connection with FIG. 7 below) whereupon gas flowing in the Reactor No. 1 Effluent sampling circuit and entering the oven box 41 at the lower left hand corner through Reactor No. 1 Effluent Inlet is switched by means of electrically-controlled switching valves (in the upper portion of box 41) to flow through the analytic instrument. When such a stream selection has been made gas will flow through box 41 in the direction indicated by arrows in FIG. 5. Only a portion of the total gas in the sampling circuit reaches the analytical instrument, the remainder being by-passed and bled off. This splitting of the total gas flow permits higher flow rates in the circuit in question and reduces gas transit times and lag in analysis so that the composition determined follows the reactor much more closely.

Gas entering box 41 through normally-open valve 27 flows by means of nipple 40 through a tee-fitting 42 and a second nipple 43 to a filter 44 labelled at a 50-micron filter. Filter 44 contains an internal cylindrical wire screen filter element (not shown) having screen openings of about 50-microns in diameter to remove any large particles which either passed through the 100 micron openings in probe screen 12 or which may have formed by coalescence after the gases entered the circuit. Tee fitting 42 also carries a drain line 45 and a normally-closed drain valve 46 which permit steam purge of filter 44, as will be described below.

From filter 44, the gases flow through outlet nipple 47 to a tee-fitting 48 carrying in its lower vertical leg a steam supply line 49 having a normally-closed, manually-operable valve 50. The upper leg of tee-fitting 48 connects through line 51 to a normally-open, manually-operable valve 52 in line 53. Closure of valves 27, 52 and opening of valves 46, 50 will effect steam back-flushing of filter 44 only. If valve 27 is also left in the open position when steam supply valve 50 is opened with drain valve 46 closed, all of the Reactor No. 1 Effluent supply circuit inclusive of filter 44 and probe 12 will be back-flushed with steam supplied from line 50.

Gases flow upwardly from tee-fitting 48 and valve 52 through line 53 to a tee-fitting 60 which is connected by a nipple 61 to a second filter 62 labelled 12-micron filter which is similar to filter 44 except that it carries an internal wire screen filter element having openings of about 12 microns in diameter. Tee-fitting 60 carries in its lower vertical leg a steam drain line 63 provided with a normally-closed, manually-operable valve 64 which serves to drain away steam and water during back-flushing of filter 62.

From the filter 62, the gases flow through a nipple 65 to a tee 66 and from thence upwardly through a normally-open, manually-operable valve 67 and line 68 to the valve switching mechanism housed in the upper compartment of box 41. Such switching mechanism will be described below.

Similarly, a steam supply line 69 and a normally-closed manually-operable valve 70 are carried in the lower vertical leg of tee-fitting 66. As with the previous filter 44, valves 52, 64 and 67, 70 permit back-flushing of filter 62 with steam without transfer of solids from filter 62 to filter 44.

The 50- and 12-micron sizes of filter mesh specified above are in no ways critical. It is preferred that two filters be employed of progressively smaller mesh in the range of 10 – 50 microns. At the location shown immediately preceding the gas switching valves, it is necessary only to remove those coarser solids which could interfere with the operation of the power-operated valves in the gas stream selector switching system. However, before any portion of the sample gases reach the analytical instrument, the gases should be filtered to remove any solid particle larger than about 5 microns in diameter. In the installation portrayed in the drawings, a guard filter (not shown) but fitted with a 1–2 micron sintered metal filter is inserted in the instrument inlet line to be described below.

GAS FLOW SWITCHING

As indicated when the Reactor No. 1 Effluent Input is energized, gases leaving filter 62 pass upwardly through line 68, the bulk of the gas flowing out of box 41 through a normally-open, manually-operable No. 1 bypass valve 80. Bypass valve 80 connects externally of box 41 with a manifold connected to a suitable waste disposal system not shown. Line 68 also has a branch 81 which connects with a solenoid-controlled valve 82 shown in the open position. The gases in line 81 thus pass through valve 82 and flow through line 83 which branches, one branch 83a supplying gas under pressure to a second solenoid-controlled valve 84 shown in the closed position thereby back-pressuring such valve to prevent leakage into No. 1 Reactor circuit being described of gases from the No. 2 Reactor Circuit described below and the other branch 83b which connects with a tee-fitting 90. Tee-fitting 90 carries in its left-hand end a bleed line 91 and in its right-hand end an instrument supply line 98 described below.

The gas leaving tee-fitting 90 divides, the bulk of it passing through bleed line 91 to a pair of solenoid-controlled valves 92, 93. Valve 92 is normally-closed when the No. 1 Reactor circuit is energized and is back-biased by the gas in line 91. Any in-leakage of gas from Stream Inlet No. 3 through line 94 (which carries a manually-operated bypass valve 95) is carried away by the gas flowing to solenoid valve 93 which is shown in the open position. Such gas flows from valve 93 through line 96 through a manually-operable, normally-open No. 3 bleed valve 97 and from thence out of box to the waste disposal system. Thus, the gas flowing to the left from tee-fitting 90 through 91 is totally exhausted from No. 1 Reactor Circuit but is also utilized to accomplish complete isolation of Stream No. 3 Inlet from the energized No. 1 Reactor Circuit.

From tee-fitting 90, the now reduced stream of gas flows to the right through instrument supply line 98 to a second tee-fitting 100 where the flow is further subdivided. Line 101 conducts the bulk of the gas flowing through line 98 to a third set of two solenoid-controlled valves 102, 103. Valve 102 is normally-closed during No. 1 circuit operation and is back biased by the gas in line 101. If leakage through valve 102 occurs the leakage gases are swept out through normally-open valve 103 and from thence through bleed line 104 through a manually-operable No. 2 bleed valve 105 and out of box 41 to the waste disposal system. Valve 102 connects through line 106 and a manually-operated No. 2 bypass valve 107 and forms a bypass for the No. 2 Reactor circuit to be described below. Thus, the bleed gases flowing through line 101 further reduce the volume of gases flowing to the instrument and are utilized to completely isolate the No. 1 and No. 2 Reactor Effluent circuits one from the other. What appears at first glance to be a somewhat complex arrangement of valves provides complete isolation of the energized No. 1 Reactor circuit from any gases which may be flowing into the box 41 through the other two gas supply inlets.

A similar valving arrangement serves to isolate the remaining sample gases flowing to the right from tee-fitting 100 from the Helium Purge Inlet located in the upper right-hand of box 41. Complete isolation is not absolutely necessary because helium is too small in mass to interfere with the operation of a mass spectrometer. Gases leaving tee-fitting 100 flow through line 110 to a fourth pair of solenoid-controlled valves 111, 112 connected in parallel. Valve 111 is in its open position whenever any of the three gas sampling circuits are energized and is closed only between analyses when the analytical instrument is being purged of sample gases with helium gas. Likewise valve 112 is closed whenever an analysis is proceed-and is opened only during periods of helium purge. Nevertheless sample gases from No. 1 Reactor flowing through valve 111 through line 113 serve to back-bias valve 112 in its closed position. Sample gases leave box 41 through line 113 and a normally-open manually-operable mass spectrometer outlet valve 114. The mass spectrometer outlet, as indicated above, is connected through a 2-micron guard filter (not shown) connected directly to the mass spectrometer instrument inlet capillary tube. The connections just described are provided with thermostatically-controlled electrical tracing and adequate insulation to insure against cooling of the gas in its travel between the heated box oven 41 and the analytical instrument.

In summary, the valve-switching system just described requires that the valves assume the following positions to accomplish feed of reactor effluent sample gases from Reactor No. 1 to the instrument:

VALVE POSITIONS
REACTOR NO. 1 EFFLUENT ANALYSIS

| Valve No. | Position | Change (1) |
|---|---|---|
| 93 | Open | No |
| 92 | Closed | No |
| 84 | Closed | Yes |
| 82 | Open | Yes |
| 103 | Open | Yes |
| 102 | Closed | Yes |
| 112 | Closed | No (2) |
| 111 | Open | No (2) |

(1) Relative to position when Reactor No. 2 Inlet is selected
(2) Valve 112 is always closed and valve 111 always open during analysis. These vales are reversed in position at end of each analysis to admit helium purge, preferably by a signal generated by means of the spectrometer back scan signal.

As indicated earlier Reactor No. 1 Effluent Input remains open throughout the analysis in question and the mass spectrometer continuously aspirates sample gas out of the circuit through line 113 and valve 114 into and through its source assembly whereby the peak amplitude D.C. signal from the spectrometer (for each constituent gas) follows the gas composition at the reactor exit very closely. If the gas composition changes during the interval of several minutes while the spectrometer is performing its scan of the various constituents, the final composition will reveal this change with great sensitivity and, moreover, the reduction, or increase in any of the principal constituents usually will spotlight for the process operators what has caused the change enabling very fast corrective action. Significant and rapid change in the effluent gas mixture while analysis proceeds results in a material accountability greater than or less than 100% alerting the operator to check for the reason and to initiate a new analysis.

When the mass spectrometer completes its programmed scan, the spectrometer issues a signal triggered by the backscan signal which causes the computer to emit a pulse which operates valve 111 to the closed position and valve 112 to the open position permitting purge of line 113 and the analytical instrument with helium gas introduced through the Helium Purge Input line 115 at the upper right hand corner of the box. In this way all of Reactor No. 1 Effluent Gases are purged from the instrument and instrument supply line 113 before another analysis is commenced.

Reactor No. 2 Effluent Input - GAS FLOW PATH

When the process operator wishes to perform an analysis on the effluent gases of the other reactor, he merely punches the appropriate push button in the Control Room Stream Selector Module (see below). This situation is portrayed in FIG. 6 of the drawings. Immediately, valve 114 is closed shutting off the flow of helium gas and valve 111 is opened to permit sample gases to flow. The remaining valves in the switching assembly just described, when energized by the same push button assume the following operating positions as shown in FIG. 5.

| Valve No. | Position | Change |
|-----------|----------|--------|
| 92        | Closed   | No     |
| 93        | Open     | No     |
| 82        | Closed   | Yes    |
| 84        | Open     | Yes    |
| 102       | Open     | Yes    |
| 103       | Closed   | Yes    |

This positioning of the valves permits gas entering box 41 through Reactor No. 2 Effluent Input to flow to the analytical instrument. As in the case just described for Reactor No. 1, the gas flows through a 50 micron filter 120, a 12 micron filter 121 and through the gas stream selector valves positioned as tabulated above. This flow path is indicated by arrows in FIG. 6 of the drawings.

The pushing of the Reactor No. 2 Effluent selector push button also sets a time delay relay (not shown) which inhibits the start of the mass spectrometer scan. Such delay relay should have a delay period of 2 to 5 minutes to allow sample gas to flow throughout the sample gas circuit including the mass spectrometer source element thereby allowing the instrument to come to equilibrium (in a compositional sense) with the new gas sample before the analytical scan commences. When its delay period has expired, the relay operates energizing the mass spectrometer to commence its mass scan.

Stream inlet No. 3 input located near the upper left-hand corner of the box as portrayed in FIGS. 4 and 5 is a spare input which is provided to analyze any other secondary gas stream in the plant. Such input can be employed to analyze the olefin supply stream for purity, the mixture of feed gases fed to each reactor, the inert gases being vented to the atmosphere, or any intermediate gas stream selected at any point in the nitrile recovery and purification system. In the system portrayed in the drawings, Stream Input No. 3 is hooked to a manually-selectable switching and manifolding system (not shown) to which sample lines are brought from all of the above and other locations in the process. Since analysis of such other gas streams are needed so much less frequently than that of the reactor effluent streams, push-button selection of such streams is not needed. Such secondary gas streams generally do not require filtering but they should be adjusted in temperature so as to minimize variations in instrument operation.

The manner in which all of the principal elements of the analytical system just described are connected together is shown diagrammatically in FIG. 7. The sample gas conditioning and stream selector module corresponding to box 41 is portrayed in the figure with the various stream inputs in the same relative positioning as shown in FIGS. 4 and 5. Line 113 connects the box 41 with the mass spectrometer instrument 130 which is connected by electrical cable 131 directly with a direct writing recording Oscillograph 132 for direct readout of gas composition. The mass spectrometer 130 also is connected by electrical conductor cable 133 with a computer interface unit 134 which converts the peaked D.C. signals from the spectrograph to binary-coded number signals which are conveyed through cable 135 to a general purpose (digital) computer 136 (for example a G.E. Model 4020). The gas composition computed by computer 136 is transmitted over cable 137 to a Process Control Room Telewriter 138 to furnish a typed record for use by Process Control Room Operators.

An optional feature shown in FIG. 7 is a means of employing the computer to furnish Secondary Gas Stream analyses. The peak signals recorded on oscillograph 132 are punched into computer cards and fed to a card punch/card reader module 139 which feeds the data directly to computer 135 over cable 140. The computer feeds the resulting composition to the telewriter 138 as described.

Other elements portrayed in FIG. 7 are paralleled stream selector switch modules, one such module 141 being located in the process control room and the other 142 being located at the mass spectrometer instrument, the latter module being convenient when analyzing secondary streams by means of the card punch/card reader module 139 and the manually-selectable secondary stream switching and manifolding system alluded to above. Also shown in FIG. 7 are the connections for Reactor No. 1 Effluent exit manifold 143, Reactor No. 2, Effluent Exit manifold 144, and Stream Inlet No. 3 exit manifold 145, all of which are, as indicated above, connected to a waste disposal system.

NITRILE PROCESS

As described in U.S. Pat. No. 2,904,580 and U.S. Pat. No. 3,308,151 unsaturated aliphatic nitriles are prepared from a 2 to 6 carbon atom aliphatic alpha-monoolefin, more preferably a 3 to 4 carbon atom aliphatic alpha-monoolefin such as propylene or isobutylene, by mixing the olefin with ammonia and oxygen or air and passing the resulting mixture of gaseous ingredients through a bed of a solid ammoxidation catalyst at reaction temperatures of from about 500° to about 1150°F. I prefer to utilize reaction temperatures between about 800° and about 950°F. In U.S. Pat. No. 2,904,580 the catalyst for such process is described as an antimony molybdate whereas in 3,308,151 the catalyst is a crystalline complex of the oxides of antimony and uranium. Other catalysts for this process based on iron or iron/bismuth compounds are said to have been employed in this same process.

While the exact nature of the ammoxidation catalyst is not critical to the present invention since the analytical and control techniques of this invention are applicable to the process conducted with any operable catalyst, I prefer to utilize the antimony/uranium oxide catalyst of the type shown in U.S. Pat. No. 3,308,151, particularly those wherein the crystalline complex of the antimony and uranium oxides is supported in or carried by an inert support such as silica and employed in a fluidized bed reactor. The method is especially applicable to produce acrylonitrile from propylene and methacrylonitrile from isobutylene.

I have found that the nitrile reaction varies more or less continuously, due in large part to the lack of reliable and precise flow control with resulting decrease in the state of oxidation of Sb/U catalysts. For the latter reason, I have found that the actual $O_2$:olefin ratio as indicated by gas flow instruments to have been fed is not to be relied on, rather the process operator should feed sufficient oxygen to insure the presence of unreacted oxygen in the effluent gas. The concentration of oxygen in the effluent indicates much more reliably whether sufficient oxygen actually existed in the catalyst bed at the locus of the reaction, such concentration of oxygen should not only be large enough to carry out the desired ammoxidation reaction but also to furnish the oxygen consumed in maintaining the catalyst at its highest state of oxidation.

Due to the highly accurate and reliable effluent gas analysis technique of this invention, I am able clearly to demonstrate for the first time that a considerably higher proportion of excess oxygen in the reactor effluent gases (than was formerly thought desirable) is, in fact, highly advantageous and for several very important reasons. Firstly, as will be shown in the examples herein, the feed of oxygen significantly in excess of that actually consumed in the reaction exerts a highly beneficial effect on the state of oxidation of the catalyst and without inordinate increase in oxygenated by-products. Highly oxidized Sb/U type catalysts are much more selective and thus tend to produce less by-products than less highly oxidized catalysts. Operation over the Sb/U catalysts at any feed ratio lower than will maintain in the effluent gases less than about 4 to 5 mol % excess oxygen usually results in a declining state of oxidation in the catalyst. When this happens, the selectivity to the desired nitrile will also decline and rapidly with continuing decline in the state of oxidation of the catalyst. At the same time, the catalyst becomes coated with carbon and/or other organic residues. A fully oxidized Sb/U catalyst of adequate surface area (in the range of 12–20 $M^2$/gram) is capable of converting over 70% of propylene per pass to acrylonitrile with minimized by-products. Even slightly reduced catalysts lower the conversion of acrylonitrile to 60% or below.

Secondly, with $O_2$:olefin molar feed ratios below those which maintain the excess oxygen in the effluent gases between about 4 and about 7 mol %, it is not possible to operate at the lower $NH_3$:olefin ratios disclosed herein without suffering significant loss of nitrile yield and possible reduction of catalyst.

One reason for the latter is that when one lowers the proportion of ammonia in the feed gases, everything else being equal, the proportion of olefin thereby is correspondingly increased forming a gas mixture of increased reducing effect. I have found that ammonia has relatively little effect on the catalyst. The two advantages of higher effluent excess oxygen levels work together very significantly to increase the long term efficiency of the process due to much longer catalyst life and easier maintenance of higher average conversion and selectivity to nitrile product, lowered raw material costs, and other reduced operating costs. Even with old catalysts not of highest efficiency, it is possible to reduce the cost of production of acrylonitrile, for example, by from at least 0.15 to 0.4 cent/lb. by operating at the low $NH_3$:olefin/high $O_2$:olefin ratios described above.

ANALYTICAL INSTRUMENTS

While the method and apparatus of this invention for conditioning the sample gases is applicable to prepare the effluent gases for any type of gas analyzer instrument, the mass spectrometer is by far the best and yields the most information with greatest accuracy. As indicated, the mass spectrometer normally operates with its source element at a very high temperature (usually 250°C) and under a very high vacuum (of the order of 1-2 × $10^{+5}$ mm Hg pressure) obviating the necessity to cool the sample gases to lower temperatures where cyanohydrin polymers may form therein.

The mass spectrometer employed preferably should be a general purpose process control instrument such as the Model 21-614-1, made by the Instrument Products Division, E. I. DuPont de Nemours Company, Monrovia, Calif. The data given herein is taken with such an instrument operated as follows:

| | |
|---|---|
| Ionizing Current - | 60 microamps |
| Scan Rate - | 5 |
| Ionizing Voltage | 68 volts |
| Source Temperature | 250°C |
| Source Pressure | 1 × $10^{-6}$ mm Hg |

The invention will now be more fully illustrated with reference to several working examples which are intended as being illustrative only.

EXAMPLE I

In this example, the operation of a pair of commercial fluid bed nitrile reactors having a combined rated capacity of about 50,000,000 lbs/year of acrylonitrile is subjected to the control system as illustrated in the drawings. Each reactor is charged with "Sohio Catalyst 21" a granular catalyst of the type described in U.S. Pat. No. 3,308,151; 3,198,750 and 3,341,471 comprising about 65%/wt. of an active crystalline complex of the oxides of antimony and uranium on a silica support. The catalyst charges employed in each reactor had been in continuous service for many months and at the start of the operation described are adjudged to be in only a moderately high state of oxidation although of a reduced surface area making them classifiable as only average performers.

At the beginning of the period described, the reactors are being operated according to the mode of operation ("Mode A" below) then thought most desirable. In such mode, the residence time is of the order of 3 to 10 seconds, the reaction temperature about 900°F and the molar feed ratio $NH_3$:propylene supposedly between about 1.15:1 and about 1.20:1 with air:propylene mol ratio supposedly about 14.5:1. A typical mass spectrometer analysis taken on the reactor effluent gases conditioned by the method of this invention is as follows:

| Component | Composition Mol% | %Conversion Based on Carbon | Based on Nitrogen |
|---|---|---|---|
| MODE "A" | | | |
| Carbon Monoxide | 1.50 | 8.72 | — |
| Carbon Dioxide | 2.07 | 12.02 | — |
| Ammonia | 1.97 | — | 27.91 |
| Water | 20.96 | — | — |
| Hydrogen Cyanide | 1.54 | 8.95 | 21.84 |
| Nitrogen | 62.58 | — | — |
| Propane | 0.10 | — | — |
| Ethane | 0.00 | — | — |
| Oxygen | 4.46(1) | — | — |

-continued

| Component | Composition Mol% | %Conversion Based on Carbon | Based on Nitrogen |
|---|---|---|---|
| Argon | 0.76 | — | — |
| Acetonitrile | 0.13 | 1.48 | 1.81 |
| Propylene | 0.43 | 7.45 | — |
| Acrylonitrile | 3.41 | 59.52(2) | 48.39 |
| Propionitrile | 0.00 | — | — |
| Acrolein | 0.07 | 1.23 | — |
| Acetone | 0.00 | — | — |
| Butene Nitrile | 0.00 | — | — |
| Benzene | 0.02 | 0.53 | — |
|  | 100.60 | 99.90 | 99.95 |

(1) Unscrubbed basis, by mass spectrometer; equivalent to about 6.1% on a scrubbed gas basis.
(2) Unscrubbed basis, by mass spectrometer; equivalent to about 70% conversion as determined by older recovery run (scrubbed gas) basis.

The above analysis indicates that the process is operating fairly well since the conversion to acrylonitrile product is about 59.5% on the basis of the spectrometer analysis but equivalent to a conversion of about 70% to acrylonitrile if it had been determined by the older recovery run procedure. The high (27.91%) residual unreacted ammonia, high (7.45%) residual unreacted propylene, and low (4.46%) residual unreacted oxygen are typical of the older high ammonia/low oxygen type of operation.

The oxygen:propylene molar ratio is increased somewhat to oxidize the catalyst more highly producing an increase in excess oxygen in the effluent gases to 5.9 mol% (unscrubbed basis by spectrometer). Simultaneously, the ammonia:propylene molar feed ratio is reduced to about 1.1:1 (theoretical 10% excess, "Mode B" below). Numerous analyses by the mass spectrometer system of this invention are taken during this mode of operation, an average or typical analysis during this period being given below.

The oxygen:propylene molar feed ratio is again increased to produce an excess oxygen content in the effluent gases of 6.5 mol% as determined by the spectrometer ("Mode C" below). Simultaneously, the ammonia:propylene feed ratio is lowered to about 1.03:1. Again numerous spectrometer analyses are performed on the reactor effluent gases by the method of this invention. The results tabulated below are average values compiled on the two experimental runs under low $NH_3$/high $O_2$ conditions:

| Conversion | Mode B $NH_3$/Propylene 1.10:1 | Mode C $NH_3$/Propylene 1.03:1 |
|---|---|---|
| Propylene to Acrylonitrile | 61.0% (1) | 60.5% (1) |
| Unreacted Propylene | 4.2% | 4.4% |
| $CO_2$ | 14.8% | 15.6% |
| Acrolein | 0.6% | 0.8% |
| Propylene/100 lb. of Acrylonitrile | 141 lbs | 141 lbs |
| Ammonia |  |  |
| Excess $NH_3$ | 18% | 14.5% |
| Converted to HCN | 23.2% | 22% |
| Converted to Acrylonitrile | 56.8% | 61% |
| $NH_3$/100 lb. of Acrylonitrile | 65.6 lb | 61.8 lb |
| Excess Oxygen | 5.9% (2) | 6.5% (2) |
| Average Temp. - °F. | 913 | 908 |
| Lbs/$H_2SO_4$/100 lbs. of Acrylonitrile | 34.0 | 26.3 |

(1) By spectrometer analysis, somewhat higher values would have been indicated by the older wet gas recovery run procedure.
(2) By mass spectrometer; equivalent to about 8% on scrubbed gases.

At the conclusion of each of the low $NH_3$/high $O_2$ experimental periods of operation described above, a sample of catalyst is taken and examined for the state of oxidation of its surface by election spin resonance according to the method of Kroenke and Carman mentioned above. In such examination, a lower ESR value indicates a higher state of surface oxidation. The data are as follows:

|  | Excess Oxygen in Effluent | |
|---|---|---|
|  | 5.9 Mol % | 6.5 Mol % |
| ESR* parameter | $1.88 \times 10$ | $1.48 \times 10$ |

*Average of ESR intensity ($I/I_o$) ratios for several of smallest particle size fractions in catalyst.

The ESR data indicate that an oxygen feed rate yielding 6.5% excess oxygen in the reactor effluent gases is slowly reoxidizing the surface of the catalyst, although the $I/I_o$ value of $1.48 \times 10^-$ indicates a surface still reduced to a significant extent. Plots of similar ESR Data over an extended period of operation at high oxygen levels indicate a steadily declining $I/I_o$ for catalysts which had been in full time service for 1 to 2 years before the high oxygen mode of operation is initiated.

Note also in the analytical data given above, that conversion of propylene to acrylonitrile is not reduced significantly by the high-oxygen, low-ammonia mode of operation while a savings of 5.8% in direct ammonia consumption is realized plus an additional savings of 22.6% in sulfuric acid consumption employed to remove unreacted ammonia from the inert vent gases. In the two periods of experimental operation at progressively lower ammonia and higher oxygen levels, the process operators perform from 5 to 10 effluent gas analyses per reactor per day according to this invention and are able to reassure themselves that conversions and selectivities continuously are maintained at high levels. While the above data is compiled with old catalyst and still better results would be obtained with newer catalyst, there is an indication that the upper limit for the oxygen:propylene feed ratio for the catalyst in question is not reached.

Formerly while operating the acrylonitrile synthesis employing the normal 2 to 3/week frequency of the older laboratory "recovery run" analysis (see text above), it is possible to detect and identify only about 40% of the operational variations and abnormalities of the process. With the analytical system depicted in the drawings, it is possible to average between 5 and 10 analyses per day per reactor identifying 90 to 96% of the departures from normal, optimum operation. In addition, accountability of raw materials and product, including by-products, is in the range of 99% or better whereas the older analytical procedures accountability seldom is better than 95 to 96%.

EXAMPLE II

Yet another advantage of the analysis system of this invention is its low lag characteristic. On one occasion, one of the fluid bed reactors of the preceding example is operating normally when a reactor effluent gas analysis is initiated at 15:00 clock time and is proceeding in normal fashion when the propylene feed is lost at time 15:10. The analysis in question is completed and typed out by time 15:27. The conversion of propylene to acrylonitrile reported in the resulting analysis is only one-third of what it had been in the previous analysis. This result allowed the process operators to detect the change, find the cause and correct it in a matter of minutes. Thus, the analytical system is shown to follow the reactor performance quite closely with little lag.

The 27-minute analysis time demonstrated in this example is a function of the speed of the computer utilized. With a faster computer, the time for analysis can be reduced to 6 to 10 minutes per analysis.

EXAMPLE III

As indicated in Example I above, it is suspected that the upper limit on oxygen:propylene molar feed ratio had not been reached. Additional periods of experimental operation of one of the commercial reactors described in Example 1 are conducted at successively higher $O_2$:propylene molar feed ratios and with various $NH_3$:propylene ratios while monitoring results with the mass spectrometer analytical system depicted in FIGS. 1 – 7 of the drawings. The data are as follows:

| $NH_3$:Propylene Molar Ratio | Excess Oxygen-Effluent (Mol %) (1) | Mol% Unreacted $NH_3$ In Effluent |
|---|---|---|
| 1.20 | 5.75 | 22 |
| 1.15 | 5.75 | 20 |
| 1.11 | 5.75 | 18 |
| 1.15 | 6.75 | 19 |
| 1.10 | 6.75 | 16 |
| 1.04 | 6.75 | 14 |
| 1.10 | 7.25 | 15 |
| 1.05 | 7.25 | 13 |
| 1.03 | 7.25 | 12 |

(1) Scrubbed gas basis; by spectrometer about 2% lower values.

The above data dramatically illustrate the necessity to increase oxygen feed rates to maintain suitably high excess oxygen levels in the range of from 4 to about 7 mol % in the reactor effluent gases. The increment in going from 5.75% excess oxygen to 7.25% of excess oxygen at a $NH_3$:Propylene ratio of from 1.2:1 to 1.03:1 permits a reduction in excess ammonia of more than 45%.

These data are achieved with only minor reductions in acrylonitrile conversion and selectivity. Similar, and in some cases still better results, are achieved at excess oxygen levels up to 7 mol % by spectrometer analysis. All of the results reported herein would be better with fresher, more efficient catalysts.

EXAMPLE IV

In this example there are compared the older recovery run analytical procedure against the mass spectrometer analysis of this invention. The data given herein is based upon statistical analysis of the data from a series of 24 comparisons wherein in each case a sample of effluent gases is collected while a mass spectrometer analysis is proceeding. Each such gas sample is analyzed by the recovery run procedure. In Column One below, there is given the gaseous component; in Column Two the average efficiency of the component in question as determined by the mass spectrometer; in Column Three, the statistical estimate of 95% limits of predictability for the mass spectrometer values of Column Two and in Column Four there are listed the corresponding recovery run efficiencies with the corresponding 95% confidence limits in brackets. The data are:

| Column One Component | Column Two Propylene Efficiencies | Column Three 95% Limits For Col. Two | Column Four Recovery Run Efficiencies (95% Limits) |
|---|---|---|---|
| HCN | 8.5 | ± 0.33% | 9.27 (± 0.92)% |
| Acetonitrile | 1.5 | ± 0.13% | 1.6 (± 0.32)% |
| Propylene | 5.0 | ± 0.66% | 4.65 (± 1.42)% |
| Acrylonitrile | 60.0 | ± 0.37 | 65.8 (± 2.04)% |

The 95% confidence limits for the mass spectrometer analysis are smaller than the inherent inaccuracies of the recovery run procedure showing that the mass spectrometer can predict recovery run efficiencies well within the reproducibility of the recovery run procedure itself.

The value of the mass spectrometer analysis is further enhanced by its speed since, with the fastest spectrometer and computer, up to six analyses per hour can be performed compared to the usual 5 – 10 hour sampling and analysis time period for each recovery run.

EXAMPLE V

Stream Inlet No. 3 of the equipment of FIGS. 1 through 7 of the drawings is utilized to perform an analysis of the purity of the propylene being fed to the reactors described in the preceding examples. Such propylene is produced by the cracking of propane. The mass spectrograph produces the following analysis:

| Ingredient | Mol % |
|---|---|
| Methane | 0.00 |
| $H_2O$ | 0.00 |
| Ethylene | 0.00 |
| Propane | 2.85 |
| Ethane | 0.05 |
| Propylene | 97.10 |
| $C_4$ Hydrocarbons | 0.00 |
| Total | 100.00 |

I claim:

1. In a method of analyzing the effluent gases resulting from an ammoxidation process wherein a mixture of an aliphatic alpha-monoolefin containing from 2 to 6 carbon atoms per molecule, ammonia and oxygen are passed through a solid ammoxidation catalyst at temperatures in the range of from about 550° to 1150°F. to produce a corresponding unsaturated aliphatic nitrile, the improvement which comprises withdrawing a portion of the gases leaving said catalyst and cooling same to a temperature in the range of from about 350° to about 450°F., removing solids larger than about 5 microns in diameter therefrom, and subjecting the resulting filtered and temperature-conditioned gas to analysis.

2. The method as defined in claim 1 and further characterized by said withdrawn portion of gases being continuous during process operation and wherein the said analysis of the resulting filtered and temperature-conditioned gases is performed by mass spectrographic analysis.

3. The method as defined in claim 1 and further characterized by said monoolefin being propylene, by said nitrile being acrylonitrile, by said withdrawal of gases being continuous and confined in a closed gas flow circuit wherein the withdrawn gas is maintained at a temperature in the range recited, by said analysis being performed by mass spectrographic analysis on gas aspirated from said circuit, and both the amount and rate of flow of said filtered and temperature-conditioned gas in said circuit being large as compared to that required for said analysis.

* * * * *